United States Patent
Dietz et al.

[11] Patent Number: 5,849,175
[45] Date of Patent: Dec. 15, 1998

[54] METHOD AND CIRCUIT ARRANGEMENT FOR ACUTATING A MEASURING SENSOR TO DETERMINE AN OXYGEN CONCENTRATION IN A GAS MIXTURE

[75] Inventors: Hermann Dietz; Werner Gruenwald, both of Gerlingen, Germany

[73] Assignee: Robert Bosch GmbH, Stuttgart, Germany

[21] Appl. No.: 809,569

[22] PCT Filed: Sep. 1, 1995

[86] PCT No.: PCT/DE95/01181

§ 371 Date: Mar. 24, 1997

§ 102(e) Date: Mar. 24, 1997

[87] PCT Pub. No.: WO96/09536

PCT Pub. Date: Mar. 28, 1996

[30] Foreign Application Priority Data

Sep. 24, 1994 [DE] Germany .......................... 44 34 194.6

[51] Int. Cl.⁶ .................................................. G01N 27/41
[52] U.S. Cl. ...................... 205/784.5; 204/425; 204/426; 205/784
[58] Field of Search ................... 204/421–429; 205/783.5, 784, 784.5, 785

[56] References Cited

U.S. PATENT DOCUMENTS

| 4,601,793 | 7/1986 | Asayama et al. .................. 204/425 |
| 4,891,122 | 1/1990 | Danno et al. ...................... 204/427 |

FOREIGN PATENT DOCUMENTS

| 427958 | 5/1991 | European Pat. Off. . |
| 3515588 | 11/1985 | Germany . |
| 4304966 | 8/1994 | Germany . |

*Primary Examiner*—T. Tung
*Attorney, Agent, or Firm*—Spencer & Frank

[57] ABSTRACT

The invention relates to a method and a circuit arrangement for actuating a measuring sensor for determining an oxygen concentration in a gas mixture, particularly in exhaust gases of internal combustion engines, wherein a detector voltage corresponding to the oxygen concentration and supplied by a reference probe is transferred into a pump voltage for a measuring probe by a circuit arrangement.

It is provided that a curve of the detector voltage ($U_D$) is used directly for determining the curve of the pump voltage ($U_P$), with a first input (38) of the circuit arrangement (36) being connected to a first input (46) of an adder (48) at whose second input (50) an add voltage is applied and whose output (54) is connected to the second input (40) of the circuit arrangement (36) via an amplifier (58).

6 Claims, 2 Drawing Sheets

METHOD AND CIRCUIT ARRANGEMENT FOR ACUTATING A MEASURING SENSOR TO DETERMINE AN OXYGEN CONCENTRATION IN A GAS MIXTURE

PRIOR ART

Measuring sensors for determining an oxygen concentration in gas mixtures, particularly in exhaust gases of internal combustion engines, are known. Such measuring sensors serve to adjust the setting of a fuel-air mixture for operating the internal combustion engine via the determination of the oxygen concentration in the exhaust gas. The fuel-air mixture may be in the so-called rich range, that is, the fuel is available in the stoichiometric surplus, which means that the exhaust gas only contains a small amount of oxygen compared to other partially unburnt constituents. In the so-called lean range, in which the oxygen of the air is predominant in the fuel-air mixture, the exhaust gas has a correspondingly high oxygen concentration. In a stoichiometric composition of the fuel-air mixture, both the fuel and the oxygen in the exhaust gas are reduced.

For determining the oxygen concentration in the exhaust gas, so-called $\lambda$ probes are known which detect a $\lambda$ value greater than 1 in the lean range, a $\lambda$ value smaller than 1 in the rich range and a $\lambda$ value equal to 1 in the stoichiometric range. In this process, the $\lambda$ probe supplies a detector voltage in a known manner, which voltage is fed to a circuit arrangement. With the assistance of the circuit arrangement, the detector voltage in known measuring sensors is transferred into a pump voltage for a measuring probe, which measuring probe is also a component of the measuring sensor and is exposed to the exhaust gas. Here, the measuring probe operates as a pump cell for which oxygen ions are pumped from a first to a second electrode of the measuring probe or vice versa, depending on the prevailing oxygen concentration in the gas mixture to be measured. Depending on whether the $\lambda$ probe detects a rich range, i. e., a $\lambda$ value smaller than 1, or a lean range, i. e., a $\lambda$ value greater than 1, it is determined via the circuit arrangement whether an electrode of the measuring probe connected to an active input of the circuit arrangement is connected as a cathode or an anode. The second electrode of the measuring probe is applied to ground so that either an anodic limiting current, in case of a rich measuring gas, or a cathodic limiting current, in case of a lean measuring gas, appears at the measuring probe. In case of stoichiometric operation, i. e., when the $\lambda$ value is equal to 1, the pump voltage is close to 0 so that there is no flow of limiting current.

The drawback of the known circuit arrangements is that, for generating the positive or negative pump voltage, a current reversing circuit must be provided which can be actuated via the detector voltage supplied by the reference probe. A measuring sensor of this type is known, for example, from German Patent 35 15 588.

SUMMARY OF THE INVENTION

According to a first aspect of the present invention there is provided a method for actuating a measuring sensor for determining an oxygen concentration in a gas mixture, particularly in exhaust gases of internal combustion engines, wherein a detector voltage corresponding to the oxygen concentration and supplied by a reference probe is transferred into a pump voltage for a measuring probe by a circuit arrangement, wherein the curve of the detector voltage is used directly for determining the curve of the pump voltage, wherein a fixed voltage is added to the detector voltage to form a voltage value which effects a shift of the detector voltage such that a stepping or transition point of the detector voltage is close to the zero point, and wherein the voltage value is amplified, and is used as the pump voltage.

According to a further aspect of the invention, there is provided a circuit arrangement for actuating a measuring sensor for determining an oxygen concentration in a gas mixture, particularly in the exhaust gas of internal combustion engines, with the circuit arrangement having a first input connected to a first electrode of a reference probe, a second input connected to a first electrode of a measuring probe, and a third input applied to ground connected to the second electrodes of the reference probe and the measuring probe, with a detector voltage of the reference probe being applied between the first and third inputs and a pump voltage for the measuring probe being supplied between the second and third inputs; and wherein the first input is connected to a first input of an adder at whose second input a fixed voltage is applied and whose output is connected to the second input of the circuit arrangement via an amplifier to provide the pump voltage.

In contrast to the known method and arrangement, the method according to the invention and the circuit arrangement according to the invention, having the features mentioned above offer the advantage that, with very simple means, a pump voltage can be obtained for actuating the measuring probe. A curve of the detector voltage is used directly for determining the curve of the pump voltage, with, preferably, a voltage value being added to the detector voltage, which voltage value effects a shift of the detector voltage such that a stepping point, i. e., the point at which a transition from the rich to the lean range occurs, of the detector voltage is close to the zero point; therefore, it is possible with a single adder to use the detection voltage directly as pump voltage for actuating the measuring probe. Complex current reversing circuits and comparator circuits and feedback circuits can be omitted. Due to the immediate, that is, direct dependence of the pump voltage on the detector voltage, a shift of the $\lambda$ value detected with the reference probe results in an automatic feedback of the pump voltage so that the appearing anodic or cathodic limiting value can be used directly as the measured magnitude for actuating a device supplying the mixing ratio of the fuel-air mixture. Since extremely few components are used for the circuit arrangement, an error deviation in the provision of the pump voltage is largely avoided.

Further advantageous features ensue from the remaining characteristics listed in the dependent claims.

The invention is described below in greater detail in an embodiment by way of the associated drawings.

DETAILED DESCRIPTION OF THE PREFERRED EMBODIMENT

Figure 1:
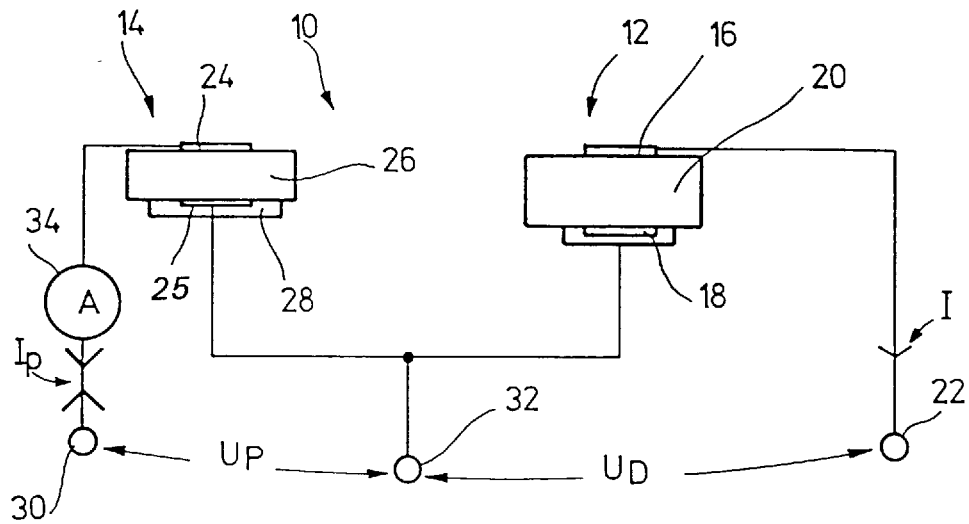
FIG. 1 is an electrical equivalent network diagram of a measuring sensor.

FIG. 1 shows an electrical equivalent network diagram of a measuring sensor for determining an oxygen concentration in a gas mixture, which measuring sensor is generally identified by 10. Measuring sensors 10 of this type are used, for example, for determining the oxygen concentration in exhaust gases of internal combustion engines to obtain a control signal for setting a fuel-air mixture with which the internal combustion engine is operated. The measuring sensor 10 has a reference sensor 12 and a measuring sensor 14. The reference sensor 12 is provided with a first electrode 16 and a second electrode 18 between which a solid electrolyte 20 is arranged. Here, electrode 16 is exposed to the gas mixture to be measured, while electrode 18 is exposed to a reference gas, for example, air. The solid electrolyte 20 is comprised, for example, of yttric oxide-stabilized zirconium oxide, while the electrodes 16 and 18 are comprised, for example, of platinum, which electrodes are sinter-fused to the solid electrolyte 20. Electrode 16 of reference probe 12 is connected to a connection 22 of the measuring sensor 10.

The measuring probe 14 is comprised of a first electrode 24 and a second electrode 25 between which a solid electrolyte 26 is arranged. Again, electrode 24 is exposed directly to the gas mixture to be measured, while electrode 25 is also exposed to the gas mixture via a diffusion barrier 28. Again, the solid electrolyte 26 is comprised, for example, of yttric oxide-stabilized zirconium oxide and the electrodes 24 and 26 are applied to the electrolyte as platinum layer. Electrode 24 is connected to a second connection 30 of the measuring sensor 10. Electrode 18 of the reference probe 12 and electrode 25 of the measuring probe 14 are interconnected and connected to a third connection 32 of the measuring sensor 10. The connections 22, 30 and 32 of the measuring sensor 10 are connected to a circuit arrangement, not shown in FIG. 1.

The following is intended to briefly explain the function of the measuring sensor illustrated in FIG. 1.

The measuring sensor 10 is exposed to a gas mixture to be measured, which mixture is applied directly to the electrodes 16 of the reference probe 12 and 24 of the measuring probe 14. Because of the oxygen concentration present in the gas mixture to be measured, an oxygen concentration differential appears at the electrodes 16 and 18 of the reference probe 12. The reference probe 12 is connected to a current source via the connection 22, with the current source supplying a constant current I. On the basis of the prevailing oxygen concentration differential, a specific detector voltage $U_D$ appears. Here, the reference probe 12 functions as a λ probe which detects whether the gas mixture comprises a high oxygen concentration or a low oxygen concentration. It is clear on the basis of the oxygen concentration whether the fuel-air mixture with which the internal combustion engine is operated is a rich or a lean mixture. In case of a change from the rich to the lean range or vice versa, the detector voltage $U_D$ drops or rises, respectively. During operation in the stoichiometric range, i. e., at a λ value equal to 1, the detector voltage $U_D$ has a stepping or transition point (FIG. 4) which characterizes the transition from the lean to the rich range or vice versa.

With the assistance of the circuit arrangement, not shown in FIG. 1, the detector voltage $U_D$ is used to determine a pump voltage $U_P$ which acts on the measuring probe 14 between the connections 30 and 32. The pump voltage $U_P$ is negative or positive depending on whether it is signalled via the detector voltage $U_D$ that the fuel-air mixture is in the rich or lean range so that the electrode 24 is connected as either a cathode or an anode. A corresponding pump current $I_P$ appears which can be measured via a measuring device 34. With the assistance of the pump current $I_P$, oxygen ions are pumped either from electrode 24 to electrode 25 or vice versa. In a stoichiometric fuel-air mixture, that is, when the detector voltage $U_D$ is in the stepping or transition point, the pump voltage is close to 0 so that there is no flow of pump current $I_P$. In a manner that does not need to be explained here in detail, the pump current $I_P$ picked up by the measuring device 34 serves to actuate a device for the setting of the fuel-air mixture with which the internal combustion engine is operated.

Figure 2:
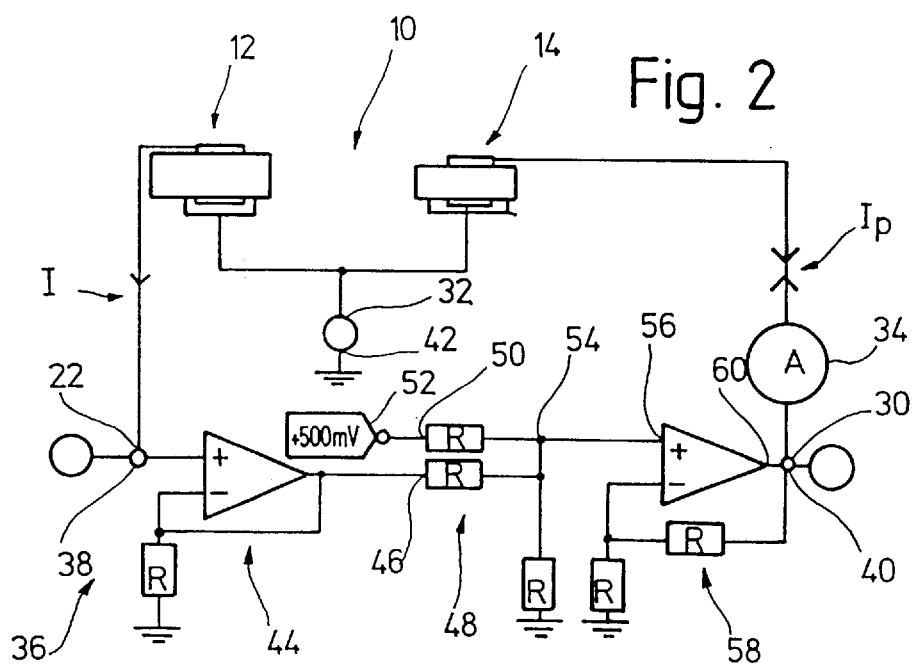
FIG. 2 is a circuit arrangement for actuating the measuring sensor.

FIG. 2 illustrates a circuit arrangement 36 to which the measuring sensor 10 is connected. Parts that are identical to those in FIG. 1 are identified by the same reference numerals and are not explained again here. The circuit arrangement 36 is provided with a first input 38 which is connected to the connection 22 of the measuring sensor 10. A second input 40 of the circuit arrangement 36 is connected to connection 30 of the measuring sensor 10. Connection 32 of the measuring sensor 10 is connected to a third input 42 of the circuit arrangement 36, which third input is applied to ground. The circuit arrangement 36 is provided with an impedance converter 44 designed as an operational amplifier whose input is connected to the first input 38 of the circuit arrangement 36. An output of the impedance converter 44 is connected to a first input 46 of an adder 48. A second input 50 of the adder 48 is connected to a constant voltage source 52 which, in the illustrated example, has a voltage of 500 mV. An output 54 of the adder 48 is connected to an input 56 of an amplifier 58 designed as an operational amplifier. The amplifier 58 is designed, for example, as two-stage amplifier. An output 60 of the amplifier 58 is connected to the second input 40 of the circuit arrangement 36 and thus to the connection 30 of the measuring sensor 10.

The circuit arrangement 36 illustrated in FIG. 2 has the following function:

A detector voltage $U_D$ is applied to the inputs 38 and 42 of the circuit arrangement 36. The detector voltage is guided via the impedance converter 44 which, according to a further embodiment variant, can also be omitted; the impedance converter effects a matching of the resistance to a low-frequency signal processing. The detector voltage $U_D$ is now applied to the first input 46 of the adder 48 to whose second input the constant voltage of 500 mV is applied. Thus, a detector voltage $U_D$, which was increased by a value of 500 mV, is applied to the output 54 of the adder 48. Via input 56, this detector voltage is now supplied to the amplifier 58, which has an amplification factor of 2 so that at the output 60 of the amplifier 58 a doubly amplified detector voltage $U_D$ is applied to which 500 mV has previously been added. This detector voltage is now applied directly, that is, without any further influence, as the pump voltage $U_P$ to the connections 32 and 30 of the measuring sensor 10. This simple processing of the detector voltage $U_D$ accomplishes that the pump voltage $U_P$ is controlled according to the curve of the detector voltage $U_D$ so that an optimum signal for the pump voltage $U_P$ is generated from the curve of the detector voltage $U_D$. By adding the 500 mV to the detector voltage $U_D$, it is ensured that the pump voltage $U_P$ is negative in the rich range so that an anodic limiting current flows across the measuring probe 14, and is positive in the lean range so that a cathodic limiting current flows across the measuring probe 14. In the range in which the detector voltage $U_D$ is in its stepping or transition point, that is, at a λ value of 1, the pump voltage $U_P$ is close to 0° so that there is no flow of pump current $I_P$.

In the following, the individual voltage curves are explained again by way of FIGS. 3 to 6.

Figure 3:
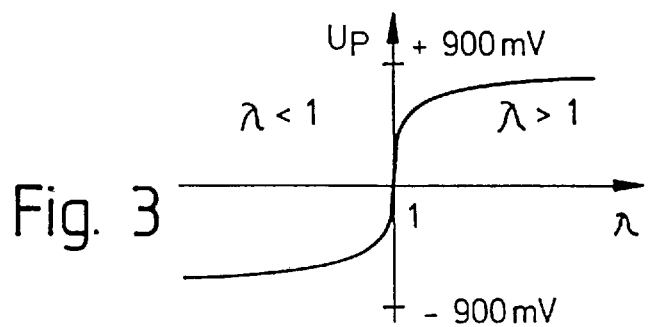
FIG. 3 shows the curve of a required pump voltage.

FIG. 3 illustrates the required voltage curve of the pump voltage $U_P$. Here, the pump voltage $U_P$ is intended to be negative in the rich range and positive in the lean range so that an anodic limiting current flows on the one hand and a cathodic limiting current $I_P$ on the other. At a λ value equal to 1, the pump voltage $U_P$ is close to the 0 range so that there is no flow of current $I_P$.

Figure 4:
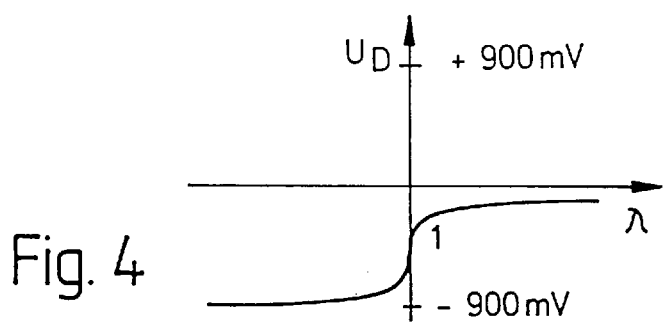
FIG. 4 shows the curve of a supplied detector voltage.

FIG. 4 illustrates the voltage curve of the detector voltage $U_D$ detected by means of the reference probe 12. This detector voltage is entirely in the negative range due to the constant cathodic current I, with the voltage curve reflecting the measured oxygen concentration differential at the reference probe 12. In the rich range, that is, in case of a lack of oxygen in the gas mixture or exhaust gas to be measured, the signal of the detector voltage $U_D$ is smaller than in the lean range in which an oxygen surplus prevails.

Figure 5:
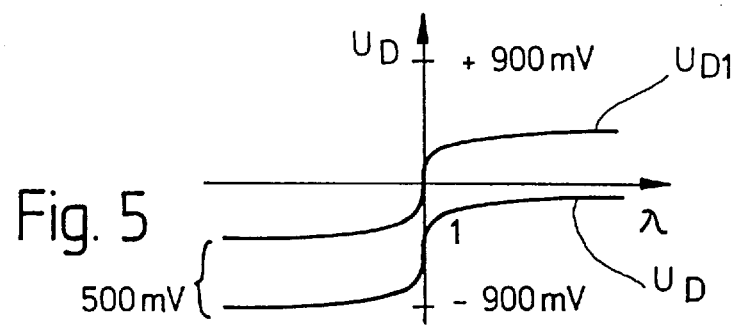
FIG. 5 shows the transition from the supplied detector voltage into an intermediate voltage.
Figure 6:
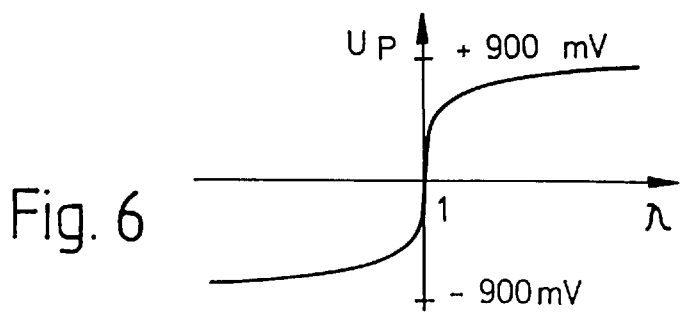
FIG. 6 shows the curve of the pump voltage generated from the detector voltage.

FIG. 5 illustrates the action of the adder 48 of the circuit arrangement 36. The constant voltage value of 500 mV is added to the detection voltage $U_D$ so that a voltage curve $U_{D1}$ is present at the output 54 of the adder 48 or at the input 56 of the amplifier 58. This voltage $U_{D1}$ is amplified twofold with the assistance of the amplifier 58 so that the voltage curve develops which is shown in FIG. 6, which corresponds to the required curve of the pump voltage $U_P$—already illustrated in FIG. 3. By means of simple addition of a constant voltage value and subsequent amplification, this pump voltage curve is now negative in the rich range and positive in the lean range. In the transition range between the rich and the lean range, the pump voltage $U_P$ is close to 0—as desired—so that there is no flow of pump current $I_P$. It becomes clear that the curve of the pump voltage $U_P$ can be taken in a simple manner from the voltage curve of the detection voltage $U_D$.

We claim:

1. A method for actuating a measuring sensor for determining an oxygen concentration in a gas mixture, particularly in exhaust gases of internal combustion engines, wherein a detector voltage corresponding to the oxygen concentration and supplied by a reference probe is transferred into a pump voltage $U_P$ for a measuring probe by a circuit arrangement, and wherein the curve of the detector voltage $U_D$ is used directly for determining the curve of the pump voltage $U_P$, wherein a fixed voltage value is added to the detector voltage $U_D$ to form a voltage value $U_{D1}$ which effects a shift of the detector voltage $U_D$ such that a stepping point of the detector voltage is close to the zero point, and wherein the voltage value $U_{D1}$ is amplified and used as the pump voltage $U_P$.

2. A method according to claim 1, wherein the fixed voltage value to be added amounts to 500 mV.

3. A method according to claim 1, wherein the amplification of the voltage value ($U_{D1}$) takes place by the factor of 2.

4. A circuit arrangement for actuating a measuring sensor for determining an oxygen concentration in a gas mixture, particularly in the exhaust gas of internal combustion engines, said circuit arrangement having a first input connected to a first electrode of a reference probe, a second input connected to a first electrode of a measuring probe, and a third input applied to ground connected to the second electrodes of the reference probe and the measuring probe, with a detector voltage of the reference probe being applied between the first and third inputs and a pump voltage for the measuring probe being supplied between the second and third inputs; and wherein the first input is connected to a first input of an adder at whose second input a fixed voltage is applied and whose output is connected to the second input of the circuit arrangement via an amplifier to provide the pump voltage.

5. A circuit arrangement according to claim 4, wherein an impedance converter is connected between the first input of the circuit arrangement and the first input of the adder.

6. A circuit arrangement according to claim 4, wherein the amplifier is a two-stage amplifier.

* * * * *